(12) United States Patent
Guarnieri

(10) Patent No.: US 12,090,151 B1
(45) Date of Patent: Sep. 17, 2024

(54) INJECTABLE SUSTAINED RELEASE BUPRENORPHINE FORMULATION

(71) Applicant: Michael Guarnieri, Baltimore, MD (US)

(72) Inventor: Michael Guarnieri, Baltimore, MD (US)

( * ) Notice: Subject to any disclaimer, the term of this patent is extended or adjusted under 35 U.S.C. 154(b) by 0 days.

(21) Appl. No.: 18/316,911

(22) Filed: May 12, 2023

(51) Int. Cl.
*A61K 31/485* (2006.01)
*A61K 9/00* (2006.01)
*A61K 47/14* (2017.01)

(52) U.S. Cl.
CPC .......... *A61K 31/485* (2013.01); *A61K 9/0019* (2013.01); *A61K 47/14* (2013.01)

(58) Field of Classification Search
CPC ..... A61K 31/485; A61K 9/0019; A61K 47/14
See application file for complete search history.

(56) References Cited

U.S. PATENT DOCUMENTS

| | | |
|---|---|---|
| 4,336,243 A | 6/1982 | Sanvordeker |
| 5,069,909 A | 12/1991 | Sharma |
| 6,375,957 B1 | 4/2002 | Kalko |
| 7,820,145 B2 | 10/2010 | Tamarkin |
| 8,093,261 B2 | 1/2012 | Guarnieri |
| 8,518,378 B2 | 8/2013 | Tamarkin |
| 9,333,180 B2 | 5/2016 | Saulnier |
| 9,333,181 B2 | 5/2016 | Benoit |
| 9,480,276 B2 | 11/2016 | Harel |
| 10,555,899 B2 | 2/2020 | Hepler |
| 2003/0060503 A1 | 3/2003 | Hamilton |
| 2007/0009502 A1 | 1/2007 | Lall |
| 2010/0144875 A1 | 6/2010 | Larson |
| 2016/0101081 A1 | 4/2016 | Pan |
| 2016/0304553 A1 | 10/2016 | Baharaff |
| 2018/0344629 A1 | 12/2018 | Hepler |
| 2020/0237653 A1 | 7/2020 | Hepler |
| 2022/0047579 A1 * | 2/2022 | Guarnieri .............. A61P 25/04 |

FOREIGN PATENT DOCUMENTS

| | | |
|---|---|---|
| WO | 8503002 | 7/1985 |
| WO | 9615815 | 5/1996 |
| WO | 0119403 | 3/2001 |
| WO | 03013476 | 2/2003 |
| WO | 03061632 | 7/2003 |
| WO | 2016055981 | 4/2016 |
| WO | WO-2022175974 A1 * | 8/2022 |

OTHER PUBLICATIONS

Guo, Food Chemistry, vol. 394, Nov. 15, 2022, 133412. (Year: 2022).*
"Abuse-Deterrent Formulations of Opioids: Effectiveness and Value", ICER, 2017, accessed through webpage, <https://icer-review.org/material/adf-evidence-report/>, accessed on Jul. 13, 2023.
"Glycerol tristearate", Hudong. Houseold Auxiliaries Co., Ltd., retrieved from the internet, <http://www.hudongha.com/products/GTS_555-43-1.htm>, retrieved on Oct. 5, 2010.
"Sterile Single-Use plastic Syringes", European Pharmacopoeia 5.0., Section 3.2.8: 314-315 (2005).
Bicket, et al., "Prescription opioids commonly unused after surgery: a systematic review", JAMA Surg., 152(11):1066-1071 (2017).
Carbone, et al., "Ethical and IACUC Considerations Regarding Analgesia and Pain Management in Laboratory Rodents", Comp. Med., 69(6):443-450 (2019).
Corncelius, "The Opioid Epidemic: What Veterinarians Need to Know", retrieved from webpage, <https://www.fda.gov/animal-veterinary/resources-you/opioid-epidemicwhat-veterinarians-need-know>, retrieved Nov. 9, 2022.
Detolla, et al., "Subcutaneous Implants of Buprenorphine-Cholesterol-Triglyceride Powder in Mice", J. Vet. Med., 2014: Article ID 365673 (2014).
Eckart, "Fat emulsions containing medium chain triglycerides in parenteral Nutrition of Intensive Care Patients", Journal of Parenteral and Eternal Nutrition, 4(4):360-366 (1980).
Guarnieri, et al., "Buprenorphine implants: a model for expedited development and approval of new drugs", Current Medical Research and Opinion, 37(1):83-88 (2020).
Guarnieri, et al., "Safety studies of post-surgical buprenorphine therapy for mice", Laboratory Animals, 49(2):100-110 (2015).
Jin, et al., "The optimal choice of medication administration route regarding intravenous, intramuscular, and subcutaneous injection", Adherence, 9:923-42 (2015).
Liu, et al."Novel depots of buprenorphine prodrugs have a long-acting antinociceptive effect," Anesth Analg. 102:1445-1451(2006b).
Morden, et al., "Racial Inequality in Prescription Opioid Receipt—Role of Individual Health Systems", NEJM, 385(4):342-343 (2021).
N.N., "Animalgesics for Mice & Rats", https://web.archive.org/web/20171115155259if_/https://www.fda.gov/downloads/AnimalVeterinary/DevelopmentApprovalProcess/MinorUseMinorSpecies/UCM373294.pdf XPO55551637 retrieved Feb. 5, 2019.
National Institute on Drug Abuse, "Overdose Death Rates", Retrieved from webpage, <https://www.drugabuse.gov/reflated-topics/trends-statistics/overdose-death-rates>, retrieved on Nov. 9, 2022.
Pontani, et al., "Disposition in the rat of buprenorphine administered parenterally and as a subcutaneous implant", Xenobiotica, 15(4):287-297 (1985).
Sailer, et al., "Medium Chain Triglycerides in Parenteral Nutrition", JPEN—Journal of Parental and Eternal Nutrition, 5(2):115-119 (1981).

(Continued)

*Primary Examiner* — Jean P Cornet
(74) *Attorney, Agent, or Firm* — PABST PATENT GROUP LLP

(57) ABSTRACT

An injectable lipid-based suspension of buprenorphine providing one to seven days of pain alleviation has been developed. A method of manufacturing an injectable buprenorphine formulation providing about two to three days of pain therapy has been developed. A method of manufacturing an injectable buprenorphine formulation providing about one to seven, preferably two to three, days of pain therapy has been developed. The formulation is made by mixing buprenorphine, glyceryl distearate, and glyceryl tristearate dry powers with a liquid medium chain triglyceride (MCT), such as MIGLYOL® 812. The buprenorphine-Glycerol di and tristearate (Bup-GDS-GTS) is provided in a range of 0.2 to 20 mg Bup-GDS-GTS to one ml (gram) MCT.

14 Claims, No Drawings

(56) References Cited

OTHER PUBLICATIONS

Shimizu, "Routes of administration", The Laboratory Mouse (2004): 527-541 (2004).
Traul, et al., "Safety Studies of Postsurgical Buprenorphine Therapy for Mice", Laboratory Animals, 49(2):100-110 (2015).
Turner, et al. "Administration of substances to laboratory animals: routes of administration and factors to consider", Journal of the American Association for Laboratory Animal Science, 50(5): 600-613 (2011).
U.S. Department of Health and Human Services, Food and Drug Administration, Center for Drug Evaluation and Research, "Abuse-Deterrent Opioids—Evaluation and Labeling, Guidance for industry", 2015, retrieved from webpage, <https://www.fda.gov/downloads/Drugs/Guidances/UCM334743.pdf>, retrieved Nov. 9, 2022.
US Centers for Disease Control, "Prescription Opioid Data", Retrieved from webpage, <https://www.cdc.gov/drugoverdose/data/prescription.html>, retrieved from the internet Nov. 9, 2022.
Zhang, et al., "Medium- and long-chain triacylglycerols reduce body fat and blood triacylglycerols in hypertriacylglycerolemic, overweight but not obese, Chinese individuals", Lipids, 45(6):501-510 (2010).
Zhang, et al., "Prescription Drug Monitoring Program Mandates and Opioids Dispensed Following Emergency Department Encounters for Patients with Sickle Cell Disease or Cancer With Bone Metastasis", JAMA, 326(3):274-276 (2021).

\* cited by examiner

INJECTABLE SUSTAINED RELEASE BUPRENORPHINE FORMULATION

FIELD OF THE INVENTION

A non-divertible partially mixed opiate analgesia for the management of acute pain in animals and humans for a period of a few days, typically two to four days.

BACKGROUND OF THE INVENTION

Pain is the primary reason patients request medical and dental care and care for their companion animals. Human and animal surgical patients generally experience acute post-operative pain only for a short duration if treated properly. The extent of post-operative pain depends on the nature of the trauma or disease, the health status of the patient, and the required surgery.

Opioids are the frontline drug for treating acute pain. Opioids act within minutes when taken orally or intravenously (IV). When used as prescribed, morphine, buprenorphine, and fentanyl and their derivatives are safe and rapidly metabolized. They have half-lives of a few hours in vivo. Because they are rapidly metabolized, opioid doses must be repeated at six to eight hour intervals to sustain pain therapy. The need for repeat dosing at three to four times daily for the two to four day periods needed to resolve acute pain has been an historical challenge in animal medicine and is a current crisis for humans.

In veterinary medicine, stresses related to restraining wounded animals for oral dosing or repeated drug injections at six to eight hour intervals have chilled the use of opiate therapy. [Carbone L. Comp Med., 2019 Dec. 1; 69(6):443-450. doi: 10.30802/AALAS-CM-18-000149]. In human medicine, the ease of taking extra opioid pills to relieve pain and divert the medication to boost affect created the opioid abuse epidemic in the US Centers for Disease Control. Prescription Opioid Data. [Retrieved from: https://www.cdc.gov/drugoverdose/data/prescribing.html.] The National Institute on Drug Abuse reported in 2019, the number of opioid-related overdose deaths has increased a staggering six-fold in 20 years. [National Institute on Drug Abuse (2019). Overdose Death Rates. Retrieved from: https://www.drugabuse.gov/reflated-topics/trends-statistics/overdose-death-rates]. Many of those with opioid use disorder (OUD) were introduced to opioids via legitimate prescriptions following injury or surgical procedure [Bicket et al. JAMA Surg.2017; 152(11): 1066-1071.doi:10.1001/jamasurg.2017.0831]. Since the ability to tolerate pain varies significantly among individuals, surgeons commonly prescribe two to three times the necessary dose of pain medication to ensure the patient has an adequate supply.

However, opioid use for post-operative pain management has become a gateway to drug addiction and diversion for illicit use. The Centers for Disease Control reported that in 2017 there were approximately 51 opioid prescriptions written for every 100 Americans. Patients leave clinics with over a billion unneeded opioid tablets per year, contributing to the current opioid epidemic. The tragic outcome of this epidemic is that the number of opioid-related overdose deaths have increased a staggering six-fold in the past 20 years.

Strategies for providing long-acting opiate therapy for animals include using off-label human transdermal fentanyl and buprenorphine patches and buprenorphine polymeric carriers. However, fentanyl patches can be removed by the patient and diverted to elicit fentanyl sales. Owners or veterinary clinic personnel can easily extract fentanyl from the patches for illicit use. The US Food and Drug Administration (FDA) has cautioned the veterinary use of opiates [https://www.fda.gov/animal-veterinary/resources-you/opioid-epidemic-what-veterinarians-need-know]. Buprenorphine polymers and patches also can be diverted. U.S. Pat. No. 8,093,261 describes an implantable pellet composed of cholesterol, glyceryl tristearate ("GTS"), and buprenorphine. When implanted into a subcutaneous ("SC") space, i.e., the surgical wound, the dissolution of the tablet yielded 2-3 days of buprenorphine analgesia [DeTolla, et al.," J. Vet. Med. vol. 2014, Article ID 365673, http://dx.doi.org/10.1155/2014/365673]. Although the tablet demonstrated safety and efficacy, animal surgeons asked for an injectable version to use when the patient had pain not related to surgery or outside of the surgical suite. The tablets also must be maintained in airtight packages to prevent cholesterol breakdown.

Guarnieri et al., developed a method to suspend the cholesterol, GTS, and buprenorphine in a medium chain triglyceride (MCT) oil to afford an injectable version of the drug. FDA registered the injectable drug Dec. 12, 2010, (MIF) number 900-008. Safety and efficacy of the drug were published by Guarnieri et al., Laboratory Animals 49(2) 100-110 (2015). The method of making and using the formulations are described in US Patent application 2020/0237653 and U.S. Pat. No. 10,555,899. Cholesterol is an essential ingredient. The extended-release properties result from a reaction between buprenorphine, cholesterol, and plasma drug transport lipoproteins.

Cholesterol oxidation is a key factor contributing to the instability of the product. Stability is limited to 18 months at room temperature. Commercial distribution is limited to approximately one year or less. The alternative is refrigerated storage, a problematic solution because buprenorphine is a Controlled Substance. Locked refrigerators are needed to store the vials. These are expensive and not routinely available.

Sources of pharmaceutical grade cholesterol can be challenged. The natural product generally is supplied as an isolate of ovine or bovine tissue. Sheep and beef tissues have been linked to "wasting" disease associated with prions. Prions are readily transmitted to humans through the food chain. Farmers may process livestock without testing for prion diseases.

Numerous long-acting depot buprenorphine injectables without cholesterol have been described. For example, injectable suspensions of buprenorphine providing 1-2 days of acute pain therapy can be prepared by dissolving buprenorphine base in food oils. [Yu, Shipeng, Development of sustained release injectable suspension dosage form of buprenorphine. The U. Tennessee, Dissertation and Theses. DAI-B 67/01 (2006) AAT 3203155.; Liu K-S, et al., Novel depots of buprenorphine prodrugs have a long-acting antinociceptive effect. Anesth Analg 102: 1445-1451 (2006)]. BRIXADI (CAM2038, Camurus AB, Lund, Sweden), a long-acting cholesterol-free phospholipid-diglyceride buprenorphine suspension for chronic, weekly to monthly OUD therapy is planned for FDA approval May 2023.

Cholesterol-free long-acting injectable biodegradable opiate depots for acute pain therapy that can be manufactured at commercial scale and are stable at room temperature are needed for human and animal pain therapy.

Human Pain Management:

The buprenorphine lipid suspension first described Guarnieri in 2010 (FDA MIF number 900-008) and recently adopted in US Patents 2020/0237653 A1 and 10,555,899 B2, is a primary solution to the current crisis. While stricter prescribing practices, monitoring programs, and even legislation work to reduce the use of opioids, morphine, buprenorphine, fentanyl, and their derivatives continue to be the mainstay of pain treatment. The FDA has emphasized the need for new pain treatments that reduce or eliminate opioid abuse liability and potential opioid diversion. This is especially important for the millions of in-patient and out-patient surgeries performed each year in the US, which expose patients to opioid analgesics that might be misused or diverted, either by the patient or their family and/or friends who could have access to medication storage. Therefore, there is an urgent need to discover medications that can provide patients with effective pain management, reduce the likelihood of diversion and overdosing, and meet the health care providers need to offer pain management without the added burden, cost, and legal implications of prescription monitoring. The availability of a safe, non-divertible opioid depot affording two-three days of powerful analgesia would provide a therapeutic solution for the pain encountered in the most common types of surgery.

Recognition that opioids are abused has a long history and is easily understood by the euphoric side effect that characterizes opioid pharmacology. Drug diversion has become a national crisis (US Food and Drug Administration. Abuse-deterrent opioids—evaluation and labeling. Guidance for industry. 2015. https://www.fda.gov/downloads/Drugs/Guidances/UCM334743.pdf (Accessed on Jun. 19, 2017)). The design of opiates that cannot be diverted has involved a significant body of research, discovery, and numerous patents, with limited success.

A search of PubMed using the terms abuse deterrent, drug formulation, and tamper resistant, and combinations of those terms generated over a thousand hits for review. A Google search using the same terms for brand name drugs and brand-named deterrent technology also produces thousands of hits, including EMBEDA®, TARGINIQ®, ERHYS-INGLA®, ERMORPHABOND®, XTAMPZA®, ERTROXYCA®, ERARYMO®, ERVANTRELA™, and ERROXYBOND® IR.

BUVIDAL®, a product approved for opioid use disorder in Europe, is made with buprenorphine, soybean phosphatidylcholine glycerol dioleate, and anhydrous ethanol. Buvidal is to treat opioid dependence (weeks, months). Buprenorphine prolonged-release injection (BUVIDAL®, CAMURUS®) is an opioid partial agonist/antagonist. It is administered subcutaneously as a weekly or monthly injection.

Patients are denied life-saving pain management therapy based on concerns by the health care provider that the patient may be a drug abuser. (JAMA 326; 274-276:2021, NEJM 385; 342-343:2021) Drug diversion includes swallowing/chewing excess tablets, crushing/grinding tablets for intranasal snorting, crushing tablets and extracting the opioid in water or alcohol for intravenous injection. Abuse deterrent formulations (ADF), including those cited above, have used five technologies: (1) addition of an aversive component, acetaminophen for example, may deter certain types of abuse including, nasal/IV use of hydrocodone/acetaminophen combinations. (2) combination with antagonist. (3) Combinations of naltrexone with morphine and naloxone with buprenorphine can decrease the euphoric rush when the tablets are crushed for IV use or snorted. (4) Combination with physical barriers that resist crushing and extraction. (5) Addition of resistant agents, polyethylene oxide to oxymorphone or a polymer matrix to oxycodone for example, to prevent tampering. (6) Addition of gelling components, sucrose acetate isobutyrate, for example, to prevent tampering.

Most of the prior art formulations are for the purpose of creating an abuse deterrent formulation ("ADF") of a generic opiate drug. A significant problem is the cost of the ADF product. In a cohort cost-benefit model, use of ADF opioids was estimated to prevent 2,300 new cases of abuse per 100,000 patients treated over five years, but to cost the health care system an additional $533 million over that time span. It was estimated that using ADF opioids costs the health care system an additional $231,500 to prevent one new case of abuse and approximately $80,500 in additional health system costs to prevent one year of abuse. Health care cost neutrality could not be achieved even when the effectiveness of ADF opioids in preventing abuse was increased to 100%, with ADF opioids still incurring an additional cost of $113 million over five years. However, cost neutrality could be achieved if ADF opioids were discounted by 41% from the current market-basket price. See Institute for Clinical and Economic Review: Abuse-Deterrent Formulations of Opioids. Effectiveness and Value. 2017. https://icer-review.org/material/adf-evidence-report/ A second problem is that the opioid can be diverted because the opiate products to treat acute pain involve polymers, tablets, and patches. Once the prescribed drug is given to the patient, or pet owner, the product can be diverted to non-prescription use.

It is an object of the present invention to provide a prolonged pain relief formulation that is resistant to extraction and abuse by a patient.

It is another object of the present invention to provide a pain relief formulation that provides opioid mediated pain relief for a period of one to four days.

SUMMARY OF THE INVENTION

A method of manufacturing an injectable buprenorphine formulation providing about two to three days of pain therapy has been developed. The formulation is made by mixing buprenorphine (buprenorphine HCl or buprenorphine), glyceryl distearate, and glyceryl tristearate dry powders with a liquid medium chain triglyceride (MCT) such as MIGLYOL® 812 (Azelis, medium-chain triglycerides extracted from endosperms of palm oil and or coconut plants, consisting of a mixture of triglycerides of saturated fatty acids, mainly caprylic acid and capric acid). The buprenorphine-lipid suspension is provided in between 0.2 and 20 mg buprenorphine-glyceryl disterates and tristearates to one ml (1 ml=1 gram) MCT.

The formulation is referred to as Buprenorphine Lipid Suspension (BLS). It is preferably administered by subcutaneous injection in an amount effective to manage pain from trauma and post-surgical acute pain in humans and animals for a period of a few days, typically two to three days. It is resistant to diversion by the patient because the buprenorphine cannot be separated from BLS because the opiate partitions evenly with the lipid matrix to form a non-divertible suspension. BLS offers health care providers and patients a safe and effective alternative to the current standard of opioid prescribing and reduces the opportunity for diversion and overdosing. The product is especially suited for clinic use in areas with elevated patient populations of the socially disadvantaged.

DETAILED DESCRIPTION OF THE INVENTION

I. Definitions

As used herein, subcutaneous refers to administration under the skin, typically by injection.

As used herein, intramuscular refers to administration by injection into the muscle.

As used herein, intraperitoneal means administration into the peritoneal cavity.

As used herein, an emulsion is a mixture of two or more liquids that are normally immiscible (unmixable or unblendable) owing to liquid-liquid phase separation. Emulsions are part of a more general class of two-phase systems of matter called colloids. Although the terms colloid and emulsion are sometimes used interchangeably, emulsion should be used when both phases, dispersed and continuous, are liquids. In an emulsion, one liquid (the dispersed phase) is dispersed in the other (the continuous phase).

As used herein, a suspension is a heterogeneous mixture of a fluid that contains solid particles sufficiently large for sedimentation.

As used herein, "half-life" refers to a pharmacokinetic parameter that is defined as the time it takes for the concentration of the drug in the plasma or the total amount in the body to be reduced by 50%. After one half-life, the concentration of the drug in the body will be half of the starting dose. With each additional half-life, proportionately less of the drug is eliminated. However, the time required for the drug to reach half of the original concentration remains constant. In general, the effect of the drug is considered to have a negligible therapeutic effect after four half-lives, that is, when only 6.25% of the original dose remains in the body.

As used herein, pain relief refers to reducing the severity and/or duration of pain or symptoms thereof.

II. Compositions

Buprenorphine

Buprenorphine is a thebaine alkaloid that is 7,8-dihydromorphine 6-O-methyl ether in which positions 6 and 14 are joined by a —$CH_2CH_2$— bridge, one of the hydrogens of the N-methyl group is substituted by cyclopropyl, and a hydrogen at position 7 is substituted by a 2-hydroxy-3,3-dimethylbutan-2-yl group.

In one embodiment, the Buprenorphine hydrochloride is the hydrochloride salt form of buprenorphine, a synthetic phenanthrene with narcotic analgesic activity. Buprenorphine hydrochloride is a partial agonist at the mu-opioid receptor and an antagonist at the kapa-opioid receptor in the central nervous system. However, under the conditions of recommended use it behaves as a classic mu-opioid agonist, mimicking the actions of endogenous peptides at CNS opioid receptors. The agonist action results in a raised pain threshold and increased tolerance to pain. However, it also may cause sedation, physical dependence, and respiratory depressant effects and decreases heart rate and blood pressure.

Buprenorphine is commercially available but is regulated as a US Drug Enforcement Agency (DEA) controlled substance.

Cholesterol Free

The formulation avoids the use of cholesterol by using a lipid molecule glyceryl (glycerol) distearate with buprenorphine in a food oil. Glyceryl distearate has a lipid distribution pattern in human and animal cells similar to cholesterol, contains a free hydroxyl group, but does not contain an oxidizable unsaturated double bond. Injections of buprenorphine HCl or buprenorphine with glyceryl (glycerol) tristearate (GTS) in the medium chain triglyceride (MCT) base seems to provide acceptable blood levels of buprenorphine for only 1-2 days. Addition of a second solid lipid, e.g., glyceryl distearate, delays the uptake of buprenorphine by the interstitial fluid, increasing plasma half-life and bioavailability for an additional one to two days.

Glyceryl Distearate (GDS) is added to the GTS, buprenorphine and then to the MCT to a final concentration of between greater than 0 and 20 mg GTS-GDS to one mL (approximately 1 gram) MCT.

Glyceryl distearate is $C_{39}H_{76}O_5$. Glyceryl distearate can be prepared by partial hydrolysis of vegetable oil consisting mainly of triglycerides of stearic acid and by esterification of glycerol with stearic acid of plant or animal origin. The product GDS in the form of the glycerol 1-2 stearic acid esters or 1-3 esters is isolated from a reaction mixture by distillation. GDS is a white or off-white waxy powder insoluble in water. It is soluble in ethanol, chloroform, and benzene.

Glycerol Tristearate is $C_{57}H_{110}O_6$. Glyceryl tristearate is prepared by reacting glycerin with stearic acid in the presence of a suitable catalyst such as aluminum oxide. It also occurs in many animal and vegetable fats such as tallow and cocoa butter. It is a white, microfine crystalline powder. It is soluble in hot alcohol, benzene, and chloroform, very slightly soluble in cold alcohol, in ether and in petroleum ether, and insoluble in water, off-white to cream powder.

Medium Chain Triglycerides

Medium-chain triglycerides (MCTs) are triglycerides with two or three fatty acids having an aliphatic tail of 6-12 carbon atoms, i.e., medium-chain fatty acids (MCFAs). There are multiple commercial suppliers of MCTs for use as excipients.

MCT is the term used to describe one form of neutral lipids, triglycerides, which contain fatty acid molecules with chain lengths from 6 to 12 carbon atoms. The manufacturing is accomplished by liberating free fatty acids from coconut or palm oil by steam hydrolysis, distillation, and esterification of the free medium chain fatty acids with glycerol. The density of MCT is 0.92-0.98 gm/mL.

MIGLYOL® neutral oils are clear, slightly yellowish esters of coconut and palm kernel oil-derived caprylic and capric fatty acids and glycerin. MIGLYOL® 810 and MIGLYOL® 812 are triglycerides of the fractionated C8 and C10 plant fatty acids. They only differ in their C8/C10-ratio. MIGLYOL® 810 has a higher C10-content, therefore its viscosity and cloud point is lower. The fatty acids used for the production of MIGLYOL® 810 and MIGLYOL® 812 comply with CFR 21 § 172.860 and are classified as GRAS. MIGLYOL® 810 and MIGLYOL® 812 are of neutral odor and taste. They are free of additives such as antioxidants, solvents and catalyst residues. They have a high stability against oxidation and are liquid at 0° C.

MIGLYOL® 812 is 50-80% Caprylic (C8:0) acid; 20-50% Caproic (C:10) acid. This is the preferred source of MCT blended with the GST and buprenorphine.

III. Methods of Manufacture

The formulation contains buprenorphine and glyceryl stearate dry powers in combination with a liquid medium chain triglyceride (MCT, MIGLYOL® 812). Buprenorphine in combination with GTS and GDS is provided in a range of 0.2 to 20 mg of buprenorphine-GTS+GDS per gram (or ml) of MCT (medium chain triglycerides, such as MIGLYOL® 812).

| Weight of Buprenorphine and glycerides per gram of MCT | | |
|---|---|---|
| Buprenorphine | GTS plus GTS glycerides | MCT |
| 0.2 to 20 mg | greater 0 to 20 mg | 1 gram |

In a typical formulation, buprenorphine GDS and GTS are added to MCT-oil containing 0.5 to 1% (v/v) benzyl alcohol preservative and 0.2 to 1% (v/v) alpha tocopherol (Vit. E, Sigma, St Louis MO) antioxidant in a container that has been fitted with paddle blender. The blender is sealed to the vessel in a manner to prevent the addition of air. The vessel is flushed with nitrogen gas sufficient to remove ambient air, sealed, and blended 4-8 hours at room temperature with a paddle (ca 500 rpm) until standard sampling confirms a homogeneous suspension.

In a preferred embodiment, the blended lipid suspension is transferred to glass vials by nitrogen pressure. The vials are crimped to provide an air-tight seal. The vials are flushed with a nitrogen blanket, sealed, and subject to sterilization by radiation. Solutions for subcutaneous injection are removed from the airtight vial with a syringe.

IV. Abuse Deterrent Formulation

This formulation is not easily diverted and abused by a patient. The health care provider injects the patient with the long-acting opioid suspension at the time of surgery or other treatment. The patient cannot remove or extract the drug after administration. Buprenorphine tightly binds to biofluids and tissue homogenates. Efforts to extract the drug in vitro lead to incomplete and variable recoveries (Pontani et al., Xenobiotica 15: 287-297; 1985).

This formulation is not easily diverted and abused by a health care provider. Doctors and nurses account for one of the highest rates of addiction in the workforce. According to USA Today, "Across the country, more than 100,000 doctors, nurses, technicians and other health professionals struggle with abuse or addiction, mostly involving narcotics such as Oxycodone and Fentanyl." (Mar. 25, 2021) The risk of abuse by health care providers is also reduced using this formulation. Absent extensive chemical manipulation, the formulation cannot be snorted. The lipid solution cannot be abused by intravenous injection because a few mL of the lipid suspension would cause intravenous occlusion and stroke. It cannot be swallowed for abuse or recreation because buprenorphine has minimum absorption in the intestine.

The drug cannot be diverted by extraction of the buprenorphine from the lipid suspension because the buprenorphine partitions with the lipid matrix. For example, efforts to isolate and analyze the amount of buprenorphine in the lipid suspension require blending 3 mL of the drug suspension, which contains 30 mg of buprenorphine, with 500 mL of methanol followed by chromatography to separate the medium chain triglyceride from cholesterol or long chain di and triglyceride, and buprenorphine.

Health care providers do not have to keep track of their opiate drug prescriptions. It gives the patient the confidence that their potential pain is being treated with a powerful and safe opioid. It solves the problem of asking patients to securely store their opiate medication and take a drug tablet at six-hour intervals for three days. It solves the pharmacology problem of rising and falling blood levels of drug during the tablet-taking intervals. In addition, it solves a problem created by giving patients opiate analgesia in tablet form. Prescription tablets are a gateway to drug addiction. Tablets can be diverted for non-prescription recreational drug abuse. A current opioid abuse crisis has been fueled by excess drug prescriptions. This formulation cannot be diverted by patients or care givers. The drug is ideally suited for in-patient dental, ob-gyn, dermatological, foot, gastrointestinal, and other surgeries.

V. Methods of Use

The formulation is administered subcutaneously, or less preferably, intramuscularly or intraperitoneally, by injection to provide approximately one to four, typically two to three, days of safe, powerful opiate analgesia for animals and humans following a single subcutaneous injection. By administering only by subcutaneous or intramuscular injection, the risks associated with injection into intravenous and intraarterial sites are avoided. Intraperitoneal sites have limited efficacy of 1-2 days.

The formulation can be administered to patients with injuries or surgical procedures, dental work, or other forms of trauma. It may also be used to treat other conditions that are treated using buprenorphine.

The administered dose is typically between 0.2 and 1 mg buprenorphine/kg of animal or human weight.

The dose can be repeated at two-to-three-day intervals for up to five repeat doses. Further dosing can be safe but is not clinically advised because the patient has likely converted from acute to chronic pain.

The efficacy of the initial dose is 1-7 days, typically 2-3 days, as measured by drug bioavailability, that is, by the concentration of buprenorphine per ml of blood. Blood concentrations demonstrating bioavailability range from 0.2 to 10 ng of buprenorphine per mL of blood. Efficacy also can be measured by quantitative sensory testing (QST). Generally, efficacy as measured by QST is 1-2 days longer that efficacy as measured by bioavailability because the drug binds to receptors that process pain signals for an additional 1-2 days.

The present invention will be further understood by reference to the following non-limiting example.

Example 1: Efficacy in Animal Model

Materials and Methods

Sustained plasma buprenorphine concentrations are predictors of analgesia. BALB/C male mice were injected SC with 0.050 mL of buprenorphine lipid suspensions described in the Table below.

TABLE 1

In Vivo Half-lives of Formulation
Plasma Buprenorphine: Cholesterol-Free
Injectable Lipid Suspensions.

| | | Post-Delivery Day, ng/ml* | | |
|---|---|---|---|---|
| Lipid (s) + buprenorphine (w:v) | Dose | 1 | 2 | 4 |
| MCT; 2:100 | 2 mg/kg | 2.1 | 1.1 | 0.6 |
| Oleic acid; 2:100 | 2 mg/kg | 0.5 | nd | nd |
| GDS, GTS, MCT; 2:5:10:100 | 2 mg/kg | 2.5 | 1.5 | 1.1 |
| Olive oil; 2:100 | 2 mg/kg | 1.5 | 1.7 | 0.9 |

*Avg, n = 3; nd = below level of detection at 0.2 ng/ml by HPLC, Stanford University (Birmingham, AL)

Results

Cholesterol-free suspensions of buprenorphine in lipid oils injected SC provided clinically significant blood concentrations of buprenorphine. These are based on data showing that sustained plasma concentrations of 0.5 to 4 ng/mL provide acute and chronic analgesia; concentrations of 0.1 to 5 ng/mL afford OUD therapy (Current medical Research and Opinion (2020) doi. 10.1080/03007995.2020.1840971.)

I claim:

1. An abuse-resistant injectable cholesterol-free suspension of buprenorphine consisting of a blend of buprenorphine, glycerol distearate (GDS), and glycerol tristearate (GTS) dry powders mixed with a liquid medium chain triglyceride (MCT), the suspension providing pain relieve for a period of days after injection, wherein 10 mg buprenorphine blended with GDS and GTS dry powders is added to one ml of MCT, with no cholesterol, and
   optionally between 0.2 and 1% of a compound selected from the group consisting of a preservative, an antioxidant, and a combination thereof.

2. The suspension of claim 1 in a dosage unit form providing between 0.2 and 1 mg buprenorphine/kg of animal or human weight.

3. The suspension of claim 1 wherein the medium chain triglyceride has the chemical formula 50-80% Caprylic (C8:0) acid; 20-50% Caproic (C:10) acid.

4. The suspension of claim 1 in a dosage unit in a syringe for injection.

5. The suspension of claim 1 providing three to four days of pain alleviation.

6. A method to provide pain relief comprising injecting the suspension of claim 1 in a dosage of between 0.2 and 1 mg buprenorphine/kg animal or human weight.

7. The method of claim 6 wherein the suspension is injected at two-to-three-day intervals for up to five repeat doses.

8. The method of claim 6 wherein the efficacy of the initial dose can be measured by drug bioavailability determined based on the concentration of buprenorphine per ml of blood.

9. The method of claim 6 producing concentrations of from 0.2 to 10 ng of buprenorphine per mL of blood.

10. The method of claim 9 wherein the suspension produces concentrations of from 0.2 to 10 ng of buprenorphine per mL of blood for a period of between one and seven days.

11. The method of claim 9 wherein the suspension produces concentrations of from 0.2 to 10 ng of buprenorphine per mL of blood for a period of between two and three days.

12. A method to make the suspension of claim 1 comprising
   a. blending 10 mg buprenorphine, glycerol distearate, and glycerol tristearate dry powders and adding the blended powder to one ml of liquid medium chain triglyceride (MCT), and
   b. optionally adding between 0.2 and 1% of a compound selected from the group consisting of a preservative, and/or a antioxidant, and a combination thereof.

13. The method of claim 12, performed in vacuo or under a nitrogen blanket.

14. The suspension of claim 1 containing comprising a compound selected from the group consisting of antioxidants, preservatives and combinations thereof.

* * * * *